(12) United States Patent
Zerkowski et al.

(10) Patent No.: US 10,327,766 B2
(45) Date of Patent: Jun. 25, 2019

(54) STAPLING DEVICE

(71) Applicant: MEDTENTIA INTERNATIONAL LTD OY, Espoo (FI)

(72) Inventors: Hans-Reinhard Zerkowski, Reihen (CH); Mark Pugh, Coolaney (IE); Adrian Moran, Ballinfull (IE); Ger O'Carroll, Castlebaldwin (IE)

(73) Assignee: Medtentia International Oy, Espoo (FI)

( * ) Notice: Subject to any disclaimer, the term of this patent is extended or adjusted under 35 U.S.C. 154(b) by 363 days.

(21) Appl. No.: 15/119,247

(22) PCT Filed: Feb. 18, 2015

(86) PCT No.: PCT/EP2015/053419
§ 371 (c)(1),
(2) Date: Aug. 16, 2016

(87) PCT Pub. No.: WO2015/124630
PCT Pub. Date: Aug. 27, 2015

(65) Prior Publication Data
US 2017/0007240 A1    Jan. 12, 2017

(30) Foreign Application Priority Data

Feb. 18, 2014 (EP) .................................. 14155506

(51) Int. Cl.
*A61B 17/122* (2006.01)
*A61B 17/128* (2006.01)
(Continued)

(52) U.S. Cl.
CPC ........ *A61B 17/0682* (2013.01); *A61B 17/064* (2013.01); *A61B 17/0644* (2013.01);
(Continued)

(58) Field of Classification Search
CPC ... A61B 17/0487; A61B 17/08; A61B 17/083; A61B 17/122; A61B 17/1227; A61B 17/128; A61B 2017/0488
(Continued)

(56) References Cited

U.S. PATENT DOCUMENTS 4,637,395 A * 1/1987 Caspar ............... A61B 17/0682
29/243.56
5,282,812 A * 2/1994 Suarez, Jr. ........... A61B 17/122
206/340
(Continued)

FOREIGN PATENT DOCUMENTS

WO    WO 2011130470 A2 * 10/2011 ........... A61F 2/2445

*Primary Examiner* — Andrew M Tecco
*Assistant Examiner* — Eyamindae C Jallow
(74) *Attorney, Agent, or Firm* — Patent Grove LLC; Tomas Friend

(57) ABSTRACT

A stapling device (100) for attaching a clip (205) to tissue is disclosed comprising a sheath (101) having a distal end (102) for delivery of said clip, a pusher unit (103, 103') being movable inside said sheath along a longitudinal direction (104) of said sheath, said distal end comprising a clip guide (105, 105') in which said clip is movable in said longitudinal direction, wherein said clip guide has a closed (G) configuration in which said clip guide is adapted to apply a restraining force on said clip so that said clip assumes a delivery shape (C), and an open (G') configuration in which said clip assumes a relaxed shape (C'), wherein said pusher unit is movable from a proximal position (P) in which said clip guide is in said closed configuration, to a distal position (P') in which said pusher unit engages said clip guide and the clip guide is in said open configuration. The clip guide comprises a first and a second clip guide arranged at radially opposite peripheries of the sheath and extending in the longitudinal direction.

21 Claims, 8 Drawing Sheets

(51) Int. Cl.
*A61B 17/068* (2006.01)
*A61B 17/064* (2006.01)
*A61B 17/00* (2006.01)

(52) U.S. Cl.
CPC ... *A61B 17/068* (2013.01); *A61B 2017/00778* (2013.01); *A61B 2017/00867* (2013.01); *A61B 2017/0645* (2013.01)

(58) Field of Classification Search
USPC .................. 227/901, 902; 606/142, 143, 157
See application file for complete search history.

(56) References Cited

U.S. PATENT DOCUMENTS

| | | | | |
|---|---|---|---|---|
| 5,382,253 | A * | 1/1995 | Hogendijk | A61B 17/1285 227/901 |
| 5,431,668 | A * | 7/1995 | Burbank, III | A61B 17/128 227/901 |
| 5,439,468 | A * | 8/1995 | Schulze | A61B 17/1285 227/901 |
| 5,497,933 | A * | 3/1996 | DeFonzo | A61B 17/0684 227/175.1 |
| 7,624,903 | B2 * | 12/2009 | Green | A61B 17/0684 227/175.1 |
| 2008/0125796 | A1 * | 5/2008 | Graham | A61B 17/0057 606/142 |
| 2009/0177277 | A1 * | 7/2009 | Milo | A61B 17/0401 623/2.36 |
| 2009/0299471 | A1 * | 12/2009 | Keranen | A61F 2/2445 623/2.37 |
| 2017/0007402 | A1 * | 1/2017 | Zerkowski | A61F 2/2445 |
| 2017/0177277 | A1 * | 6/2017 | Laden | G06F 3/0659 |

* cited by examiner

STAPLING DEVICE

FIELD OF THE INVENTION

This invention pertains in general to the field of devices for attaching clips to tissue. More particularly the invention relates to a stapling device for fixating clips to heart valve tissue and fixating the position of an annuloplasty device such as an annuloplasty ring to heart valve tissue, and a method therefore.

BACKGROUND OF THE INVENTION

Diseased mitral valves frequently need repair to function properly. The mitral valve leaflets or supporting chordae may degenerate and weaken or the annulus may dilate leading to valve leak (valve insufficiency). Mitral valve repair is frequently performed with aid of an annuloplasty ring or helix, used to reduce the diameter of the annulus, or modify the geometry of the annulus in any other way. In some procedures the annuloplasty ring is fixated around the annulus of the valve.

U.S. Pat. No. 8,603,161 discloses a device for attaching a prosthesis, having a slide that is pushed against a substantially horizontal anvil to cause legs of a clip to rotate outwards. The anvil can be slid out of the way so that the clip is released from the device.

EP0826340 discloses a clip device comprising a body having a substantially tubular shape. Two flaps are positioned at the end of the body receiving the clip. The flaps may pivot at the flexible portion. The other end of each flap is positioned between the legs of the clip, and keeps the legs spaced apart. When the pusher is advanced and pushing the clip out of the body the flaps are moved from the position between the legs of the clip, so that the clip may assume the heat-set predefined shape.

A problem with the prior art is the complexity of the devices which requires a several operating steps in which the several movable parts must be engaged in sequence. The procedure thus becomes more complicated and time consuming. Complex devices that are expensive to manufacture also lead to loosing the advantage of using disposable single use devices. A further problem with prior art is lack of stability between the clip position relative the catheter. It is important to be able to attach the clip at the desired site with high accuracy, which can be compromised if the clip can not be held in a controlled position before engaging the tissue. Frequently the target site may be of complex anatomy and there may be movement, such as the motion of the beating heart in addition to the operator's movements, that lead to difficulties in positioning a clip when having such lack of stability.

Further, devices and clips in the prior art are not suitable for annuloplasty implants such as helix rings that are to be positioned on either side of a heart valve. Such device would not provide sufficient fixation of such implant and lead to traumatic effects since the fixation structure must ensure the correct position of the device over time.

The above problems may have dire consequences for the patient and the health care system. Patient risk is increased.

Hence, an improved stapling device for attaching annuloplasty implants such as helix rings would be advantageous and in particular allowing for ensuring long-term functioning, less complex procedure, and less traumatic effects on the anatomy and increased patient safety. A kit with a stapling device and a clip for providing such improvements, and a related method would also be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a stapling device for attaching a clip to tissue is provided. The stapling device comprises a sheath having a distal end for delivery of the clip, and a pusher unit being movable inside the sheath along a longitudinal direction of the sheath. The distal end comprises a clip guide in which the clip is movable in the longitudinal direction, and the clip guide has a closed configuration in which the clip guide is adapted to apply a restraining force on the clip so that the clip assumes a delivery shape, and an open configuration in which the clip assumes a relaxed shape. The pusher unit is movable from a proximal position in which the clip guide is in the closed configuration, to a distal position in which the pusher unit engages the clip guide and the clip guide is in the open configuration. The clip guide comprises a first and a second clip guide arranged at radially opposite peripheries of the sheath and extending in the longitudinal direction.

According to a second aspect of the invention a stapling kit is provided comprising a stapling device according to the first aspect of the invention and a clip having a delivery shape in which the legs are substantially parallel, and a relaxed shape wherein the legs cross each other.

According to a third aspect of the invention a system is provided comprising a stapling device according to the first aspect of the invention and a clip according to the second aspect of the invention, and a helix-shaped implant having a first and second ring adapted for positioning on either side of heart valve tissue.

According to a fourth aspect of the invention a method of releasing a clip from a stapling device is provided comprising providing a pre-loaded clip in the stapling device having a sheath and a clip guide at a distal end of the sheath, moving a pusher unit inside the sheath from a proximal position to a distal position to engage the clip guide in which the clip is movable in a longitudinal direction of the sheath, wherein moving the pusher to the distal position comprises moving the clip guide from a closed configuration, in which the clip guide is adapted to apply a restraining force on the clip so that the clip assumes a delivery shape, to an open configuration in which the clip assumes a relaxed shape, whereby when the clip is in the relaxed shape the clip is released from the stapling device.

According to a fifth aspect of the invention a clip for use in a system according to the third aspect of the invention is provided. The clip comprises legs and has a delivery shape and a relaxed shape, wherein the legs, in the relaxed shape, have a proximal portion where the legs are substantially parallel along a proximal length corresponding to at least the sum of the diameters of a first and a second ring of a helix-shaped implant positioned on either side of heart valve tissue, and a distal portion that has an angle relative the proximal portion so that the legs cross each other.

According to a sixth aspect of the invention a method of delivering a clip to a target site from a stapling device is provided comprising providing a pre-loaded clip in the stapling device having a sheath and a clip guide at a distal end of the sheath, navigating the sheath to the target site such as a heart valve, attaching a part of the clip to the target site for fixating tissue and/or fixating an implant, such as an annuloplasty ring to tissue, moving a pusher unit inside the sheath from a proximal position to a distal position to engage the clip guide, wherein moving the pusher to the distal position comprises moving the clip guide from a closed configuration, in which the clip guide is adapted to apply a restraining force on the clip so that the clip assumes a delivery shape for attaching said part of the clip, to an open configuration in which the clip strives towards a relaxed shape where legs of the clip has a crossed configuration, wherein moving the clip guide comprises attaching a remaining part of the clip to the target site, and whereby when the remaining part of the clip is attached to the target site, the clip strives to the relaxed shape and applies a compressive force to the tissue and/or implant for fixating the tissue and/or implant, and releasing the clip from the stapling device.

Further embodiments of the invention are defined in the dependent claims, wherein features for the second and subsequent aspects of the invention are as for the first aspect mutatis mutandis.

Some embodiments of the invention provide for securing long-term functioning and position of an annuloplasty implant.

Some embodiments of the invention provide for less complex fixation procedures of an annuloplasty implant.

Some embodiments of the invention provide for a reduced risk of damaging the anatomy such as the CS.

Some embodiments of the invention provide for secure fixation of annuloplasty implants while ensuring an atraumatic procedure.

Some embodiments of the invention provide for less complex and easier to manufacture devices, such as single use devices, for securing clips to tissue.

Some embodiments of the invention provide for secure fixation of an annuloplasty implant on either side of a heart valve.

Some embodiments of the invention provide for increased stability of the clip relative the catheter to attach the clip with high accuracy.

Some embodiments of the invention provide for increased accuracy when attaching a clip to a beating heart.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
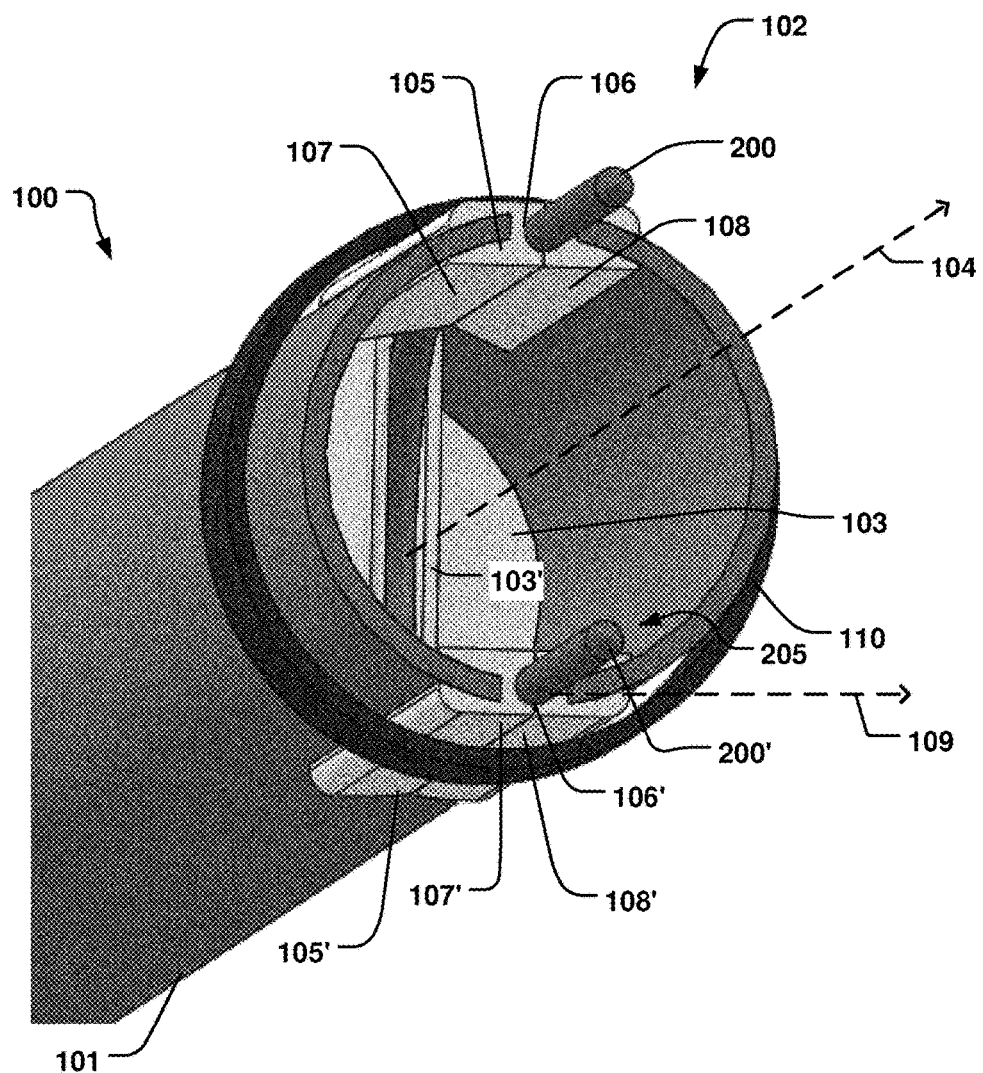
FIG. 1 is an illustration of a stapling device and a clip according to embodiments of the invention.
Figure 2:
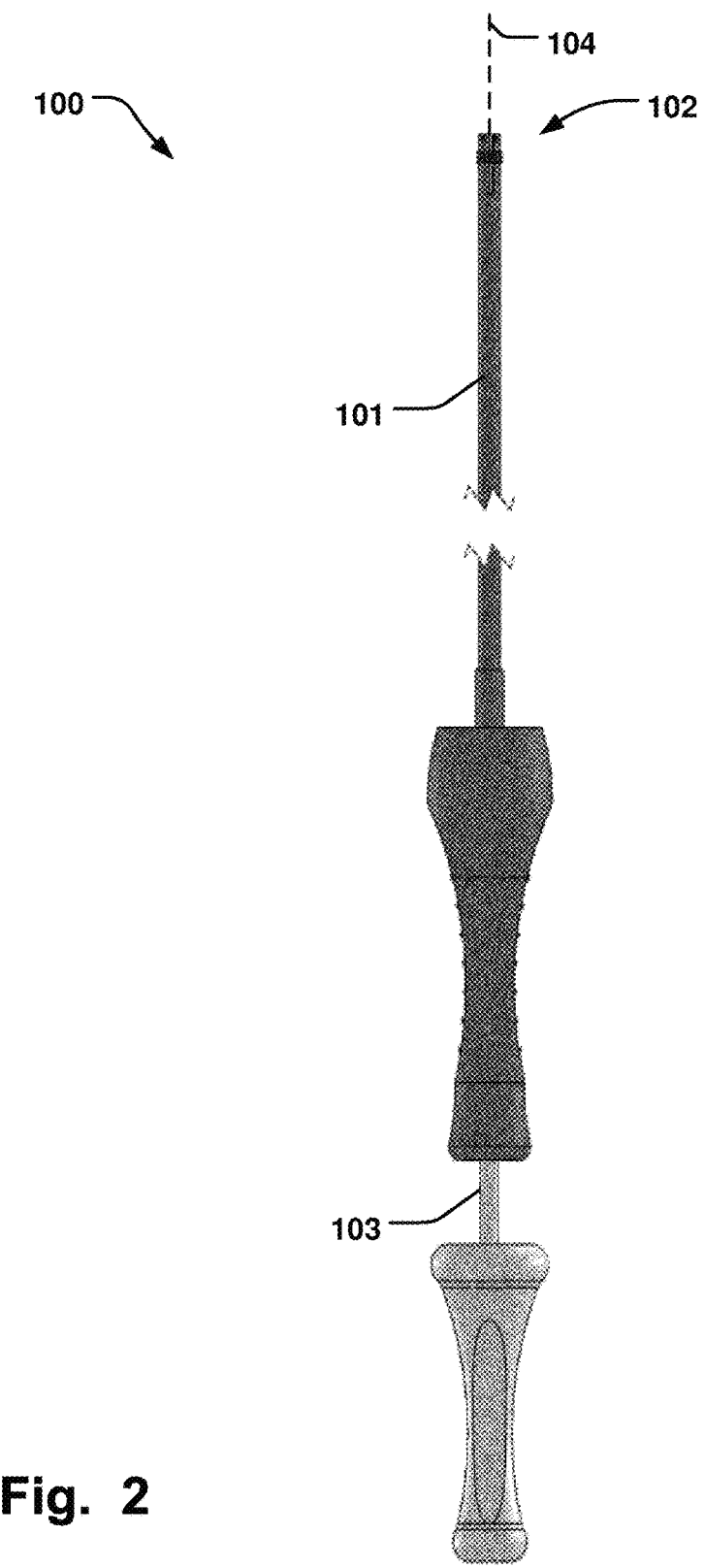
FIG. 2 is an illustration of a stapling device according to embodiments of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to fixation of annuloplasty implants to valve tissue. However, it will be appreciated that the invention is not limited to this application but may be applied to many other procedures involving attachment of clips to tissue, including for example fixation of other medical implantable devices or stapling parts of tissue together, in any medical procedure.

FIG. 1 is an illustration of a stapling device 100 for attaching a clip 205 to tissue comprising a sheath 101 having a distal end 102 for delivery of the clip, and a pusher unit 103, 103', being movable inside the sheath along a longitudinal direction 104 of the sheath. The distal end comprises a clip guide 105, 105', in which the clip is movable in the longitudinal direction. The clip guide has a closed (G) configuration in which the clip guide is adapted to apply a restraining force on the clip so that the clip assumes a delivery shape (C). The closed configuration of the clip guide 105, 105', and the delivery shape of the clip 205 are illustrated in FIGS. 1, 3, 4a, 5a, 6b. The clip guide 105, 105' also has an open (G') configuration in which the clip 205 assumes a relaxed shape (C'). The open configuration of the clip guide 105, 105', and the relaxed shape of the clip 205 are illustrated in FIGS. 4b, 5b, and 7a-b. In particular, FIGS. 4a-b and 5a-b illustrate the closed and open configurations, denoted G and G', of the clip guide, and the respective delivery shape and relaxed shape, denoted C and C', of the clip. The pusher unit 103, 103', is movable from a proximal position (P) in which the clip guide is in the closed configuration, see FIGS. 4a and 5a, to a distal position (P') in which the pusher unit 103, 103', engages the clip guide 105, 105', and the clip guide is in the open configuration, see FIGS. 4b and 5b.

By a single step movement, of the pusher 103, 103', from the proximal position (P) to the distal position (P') the clip 205 is transferred from the delivery shape to the relaxed shape. If the clip 205 is inserted into the tissue in the delivery shape it can thus be conveniently and quickly transferred to towards the relaxed shape, in which it may clamp the tissue and fixate the position of e.g. an implant such an annuloplasty implant. The single step movement also provides for a simple and inexpensive device to manufacture, which also can be made as a single-use disposable device. The clip 205 may be preloaded into the sheath 101. Since the clip 205 has its delivery shape already when the pusher 103, 103', is in the proximal position there is no additional action needed to engage the clip 205 to transfer it into the delivery shape. This also allows for achieving improved stability in the longitudinal direction 104 as explained below when the clip 205 is in the delivery shape, and allowing for further guiding in the longitudinal direction 104 when the pusher is engaged to the distal position.

Thus, by having a clip guide 105, 105', in which the clip 205 is movable in the longitudinal direction 104 of the sheath, while being transferred from the closed to the open configuration, the position of the clip in the longitudinal direction 104 can be ensured to thereby attain high stability and accuracy when positioning of the clip 205 in the delivery shape until the clip is fixated in the relaxed shape. For example, as exemplified in FIGS. 4a-b, and 5a-b, when the pusher 103' moves from the proximal position (P) to the distal position (P'), the clip 205 moves in the longitudinal 104 direction in the clip guide 105, 105'. In the proximal position of the pusher (FIG. 4a, 5a), when the clip 205 is restrained to assumes its delivery shape, the clip 205 can be positioned in the tissue due to the legs 200, 200' extending well outside the clip guide 105, 105. In this configuration, the clip guide holds the clip securely, since it functions as a guide in the longitudinal direction, so that the clip can be inserted into tissue without tilting or otherwise dislocate relative the longitudinal axis 104. As the pusher 103' moves to the distal position (FIG. 4b, 5b) the clip guides 105, 105', guides the clip 205 in the longitudinal direction, maintaining a stable delivery path, while the clip assumes the relaxed shape. The stable delivery path in the longitudinal direction 104 make sure that there is no uncertainty in the position of the clip relative the sheath, crucial e.g. when operating in difficult conditions. The relaxed shape of the clip 205 may be determined by heat treatment procedure, and the clip may be formed of a nitinol or another suitable material for heatsetting. The clip 205 may not fully assume its relaxed shape when inserted into tissue due to the counter force exerted from the tissue on the clip, but the clip will strive to the relaxed shape which results in a compressive force between the clip and tissue.

The clip guide 105, 105', may comprise a clip track 106, 106', being arranged to partly enclose a leg 200, 200', of the clip 205 and apply the restraining force previously mentioned and thereby align the clip in the longitudinal direction 104 when the clip guide is in the closed configuration. Hence, when the clip is in the delivery shape, the clip track 106, 106', of the clip guide may force the leg, or legs 200, 200', of the clip 205 into a certain position such as in the longitudinal direction. The clip tracks 106, 106, may thus also be aligned in this direction. However, it is conceivable that the clip tracks 106, 106', may have an angle relative the longitudinal axis 104 in certain applications in order to be able to deliver the clip in a certain angle relative the sheath. By having a clip track 106, 106, an improved alignment of the clip can be provided so that it follows a desired path when being transferred from the delivery shape in which the legs are restrained, to the relaxed shape. Upon moving the pusher 103' to the distal position, and transferring the clip to the relaxed shape, the clip tracks 106, 106', may continue to steer the legs 200, 200', of the clip 205 in the desired path, even if the clip tracks 106, 106', do not fully enclose the legs 200, 200', of the clip 205. The pusher 103' may be shaped to pass through, between or at the side the clip tracks 106, 106', while latter still provide guiding of the clip along the desired path.

Figures 4A, 4B:
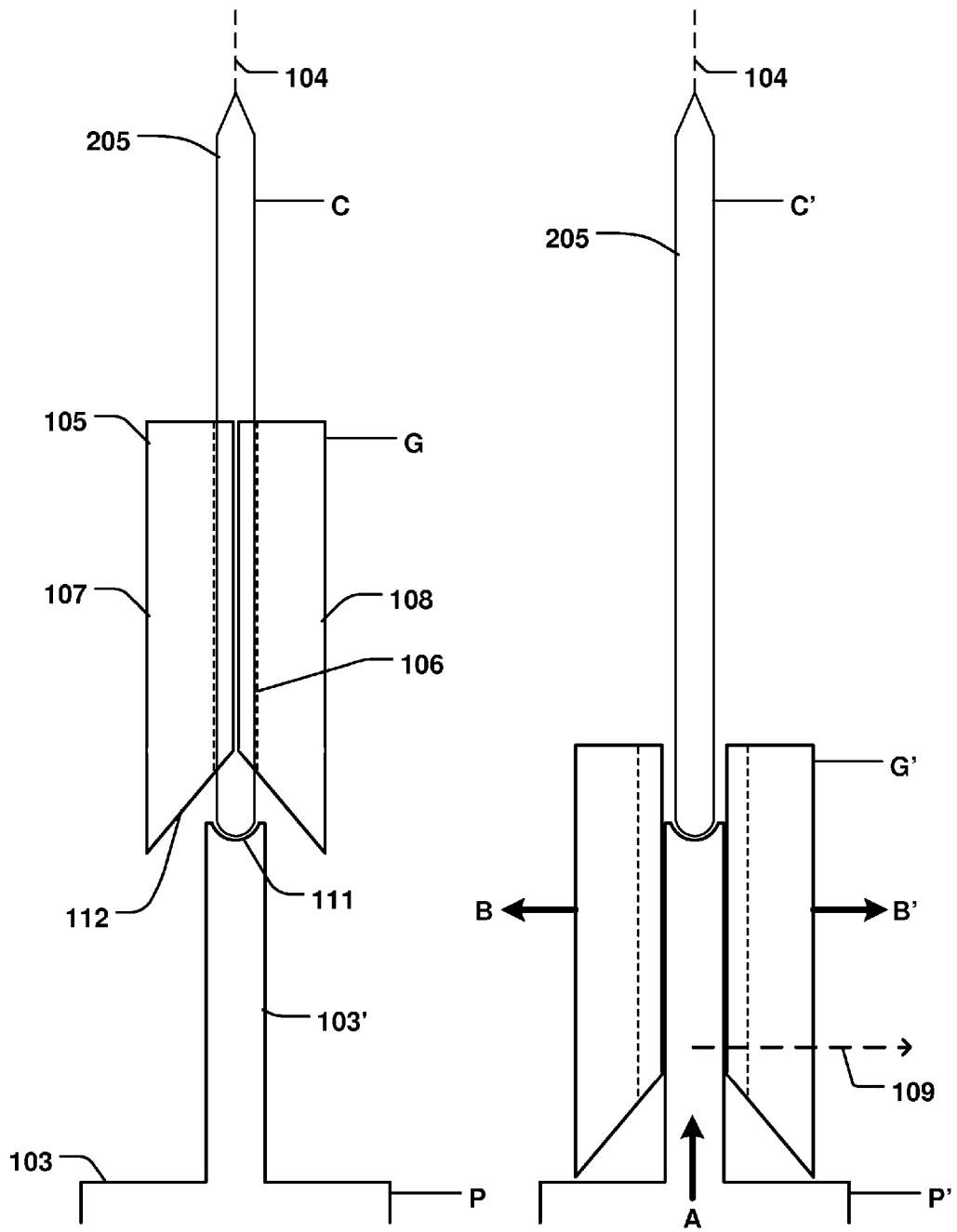
FIGS. 4a-b are illustrations of a stapling device and a clip according to embodiments of the invention.
Figures 5A, 5B:
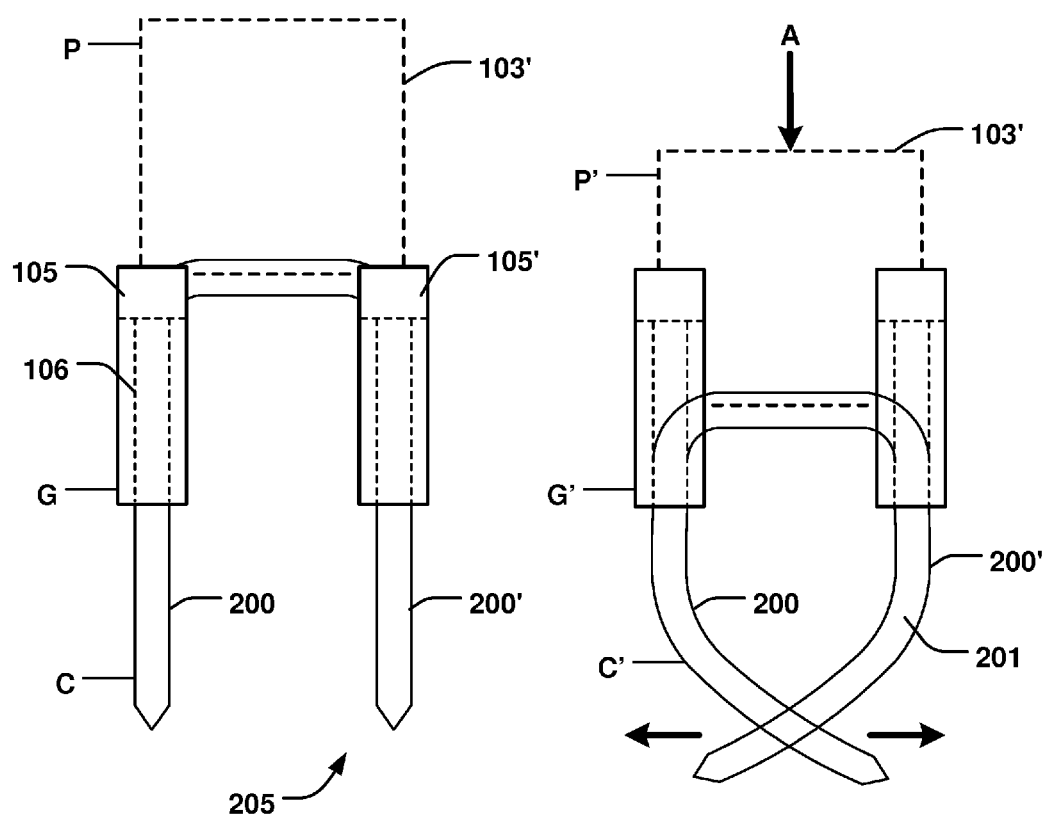
FIGS. 5a-b are side-view illustrations of FIGS. 4a-b of a stapling device and a clip according to embodiments of the invention.
Figure 6A:
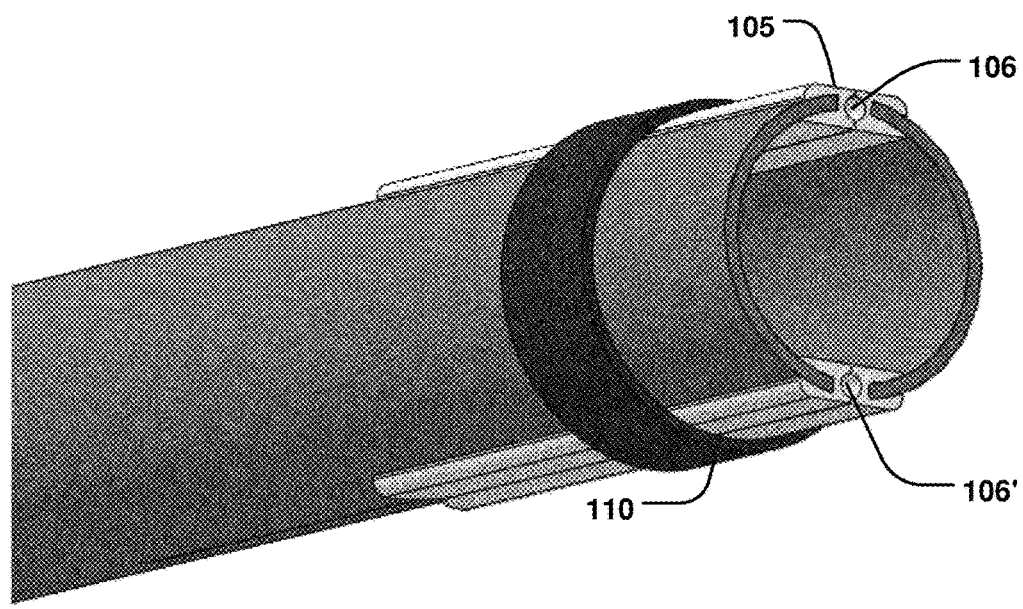
FIGS. 6a-b is an illustration of a stapling device and a clip according to embodiments of the invention.
Figure 6B:
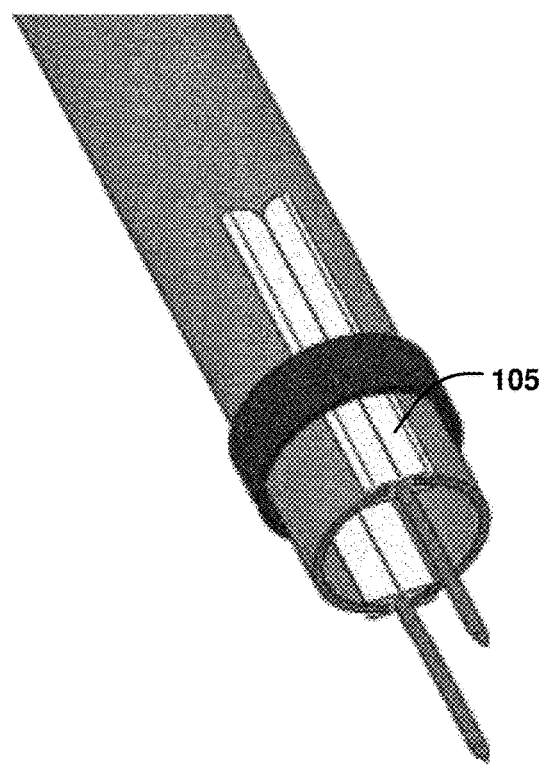

The clip guide 105, 105', may comprise two guide parts 107, 108, 107', 108', being separable in opposite directions B, B' and in directions perpendicular to the longitudinal direction 104, see FIG. 4b. The separation of the two guide parts 107, 108, 107', 108', removes the restraining force on the clip so that the clip can assume its relaxed shape. This provides for particularly improved functionality for transferring the clip 205 from the delivery shape to the relaxed shape. For example, by having two guide parts 107, 108, of the clip guide 105 that are separable in opposite directions, the force and also the range of movement required to release the restraining force on the clip may me reduced since each of the guide parts has to travel a smaller distance when being moved from the closed to the open configuration. The symmetric action also reduce the risk of undesired displacement in a particular direction transverse to the longitudinal axis 104 when the restraining force on the clip is released.

The pusher unit 103' may in its distal position G' separate the two guide parts 107, 108, 107', 108' in the mentioned opposite directions B, B', whereby the clip guide 105, 105', assume its open configuration, see FIG. 4b. This allows for simultaneously moving the clip 205 along the longitudinal axis 104 with the pusher, i.e. further into the tissue at the target site, and moving the clip guide from the closed to the open configuration so that the clip can assume the relaxed shape C' to clamp the tissue, and/or securely attach an implant to the tissue. Attaching a clip 205 and fixating tissue and implant in such single step movement provides for a quicker and easier procedure. The force acting on the pusher 103' both drive the clip forward and transfers the clip from the delivery shape to the relaxed shape in a continuous motion. In contrast to prior art, there is accordingly no need to first apply a force onto the clip with a pusher in order to transfer the clip from a relaxed shape to a delivery shape, insert the clip, and then apply a second force in a different direction to the device in order to release the clip to the relaxed configuration while the pusher is already acting on the clip with the first force. The latter example implies a more complicated device that also results in that the total force applied on the stapling device is increased, e.g. both due to the added second force, and due to that the second force must be sufficiently large to overcome the first force acting on the clip, since the forces are counteracting. This leads to an increase in frictional force against the clip, and such counteracting forces that the operator must apply to the device makes handling less precise. Sensibility to movements e.g. of the surrounding anatomy is decreased in such previous devices. This is resolved with the single-step movement with a pusher force that acts to achieve the two functions as described above.

The two guide parts 107, 108, 107', 108' may be separable in directions B, B' along a tangent line 109 to the sheath 101, see FIG. 4b. This allows for maintaining a compact profile of the sheath 101 (FIG. 1) even when the clip guide 105, 105', is in the open position, since the movement is contained as close to the periphery of the sheath 101 as possible.

The two guide parts 107, 108, 107', 108' may each comprise a clip track 106, 106', arranged on either side of a leg 200, 200', of the clip 205 to apply the mentioned restraining force and align the clip 205 in the longitudinal direction 104 when the clip guide 105, 105', is in the closed configuration. By retaining the clip on each side of the leg in a clip track the precision in the alignment of the clip is improved, since it is possible for the two guide parts to partly enclose the clip on either side of the leg.

The clip guide 105, 105', may be resiliently movable from the closed configuration to the open configuration. This provides for a smooth and predictable resistance acting on the movement of the pusher 103' when engaging the clip guide. This allows for a controlled action when moving the clip from the delivery shape to the relaxed shape and a controlled release. The stapling device 100 may comprise a resilient unit 110 arranged to apply the resilient force on the clip guide 105, 105', see FIG. 1. The resilient unit 110 may be provided at the periphery of the sheath 101 and contacting the clip guide 105, 105', to counteract movement thereof with a predefined resistance that can be adjusted by varying the resilience or flexibility of the resilient unit 110. FIG. 1 illustrates a resilient unit 110 provided radially outside the clip guide 105, 105', to apply a counteracting force radially inwards. The resilient unit 110 may be a ring of flexible material such as silicone or other flexible polymer, or wires of a flexible alloy or fabric.

Figure 3:
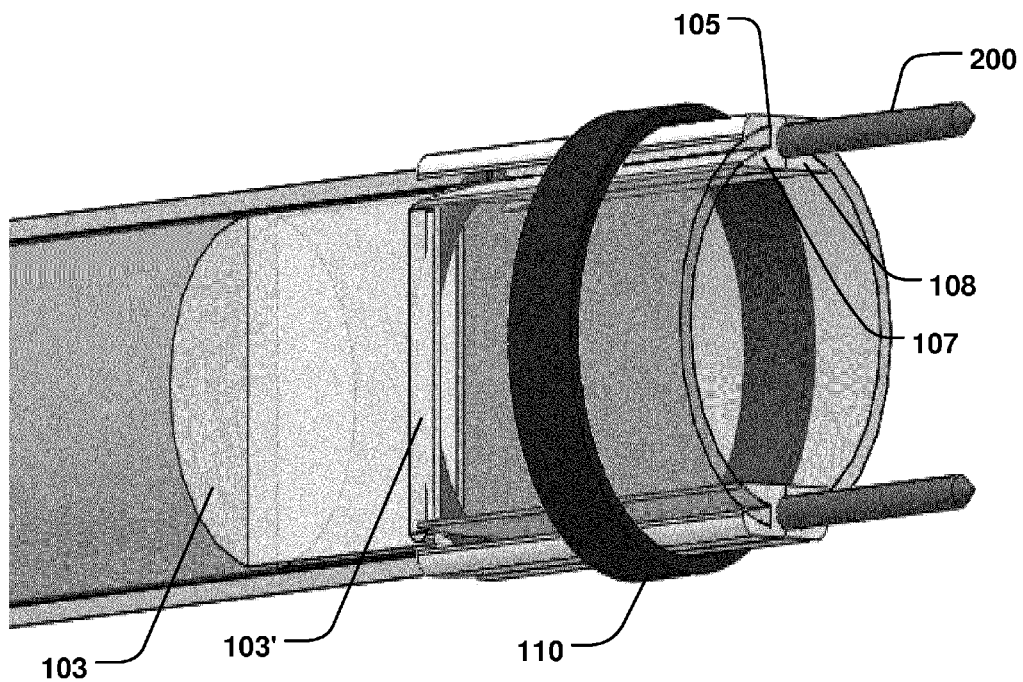
FIG. 3 is an illustration of a stapling device and a clip according to embodiments of the invention.

The pusher unit 103 may comprise a distal tongue 103' arranged to push the clip 205 through the clip guide 105, 105', in the longitudinal direction 104 and move the clip guide 105, 105', from the closed configuration (G) to the open configuration (G'), see FIGS. 3 and 4a-b. Hence, it provides for moving the clip 205 along the longitudinal axis 104 with the pusher and simultaneously moving the clip guide from the closed to the open configuration so that the clip can fixated in the relaxed shape C'. A narrow distal tongue 103' allows for a compact design of the clip guide even in the open configuration, and the tongue 103' will only displace the clip guide a small distance relative the diameter of the sheath 101 to maintain a compact profile.

The distal tongue 103' may engage an angled surface 112 of the clip guide 105, 105', relative the longitudinal direction 104 when the pusher unit 103' is moved from the proximal position (P) to the distal position (P'), so that the clip guide is moved from the closed configuration (G) to the open configuration (G'), see FIG. 4a. The angled surface 112 allows the tongue 103' to easily slide into the correct position and move through the clip guide 105, 105', which improves precision of the and device 100. It also provides for a more gradual transition from the closed to the open configuration as the angled surface 112 slides against the pusher 103' with gradual displacement in the radial direction. The clip 205 can thus be moved from the delivery shape to the relaxed shape more gradually as it advances along the longitudinal axis 104. This may be desired in certain situations where it is desired to delay the movement of the clip 205 to the relaxed shape.

The distal tongue 103' may be arranged for engagement with the clip 205 at an engagement surface 111 having a recess to receive a portion of the clip 205. This provides for increasing the radial stability of the clip as the recess 111 prevents movement in the radial direction.

The clip guide 105, 105', may comprise a first 105 and a second 105' clip guide arranged at radially opposite peripheries of the sheath 101 and extending in the longitudinal direction 104. This is illustrated in the exemplary embodiment of FIG. 1, and allows for improved accuracy in guiding the clip 205 when moving the clip forward by ensuring guiding at both sides of the clip being positioned radially across the sheath 101. Tilting or other dislocation of the clip is prevented. The first and second clip guides 105, 105', may be being arranged to partly enclose a first 200 and a second 200' leg of the clip, respectively, and align the clip in the longitudinal direction 104 when the clip guide is in the closed configuration. This further improves the positioning of the clip at the peripheries of the sheath 101. Each of the first and second clip guides 105, 105', may comprise two separable guide parts 107, 108, 107', 108' as illustrated in FIG. 1.

The pusher unit 103' may simultaneously engage the first and second clip guides 105, 105', when moved from the proximal position (G) to the distal position (G'), whereby the two separable guide parts 107, 108, 107', 108' of each of the first and second clip guides are separated to assume the open configuration. This provides for stabilizing both legs 200, 200', of the clip to simultaneously as the clip is pushed through the clip guide.

Stapling kit according to one embodiment is disclosed, see e.g. FIG. 1, comprising a stapling device 101 as described above and a clip 205 having legs 200, 200'. The clip 205 has a delivery shape (C) in which the legs are substantially parallel, and a relaxed shape (C') wherein the legs cross each other, see FIG. 5b. The crossed legs allows for increasing the strength of the fixation of an implant such as an annuloplasty ring to tissue, and preventing dislocation by locking the implant in place.

Figure 7A:
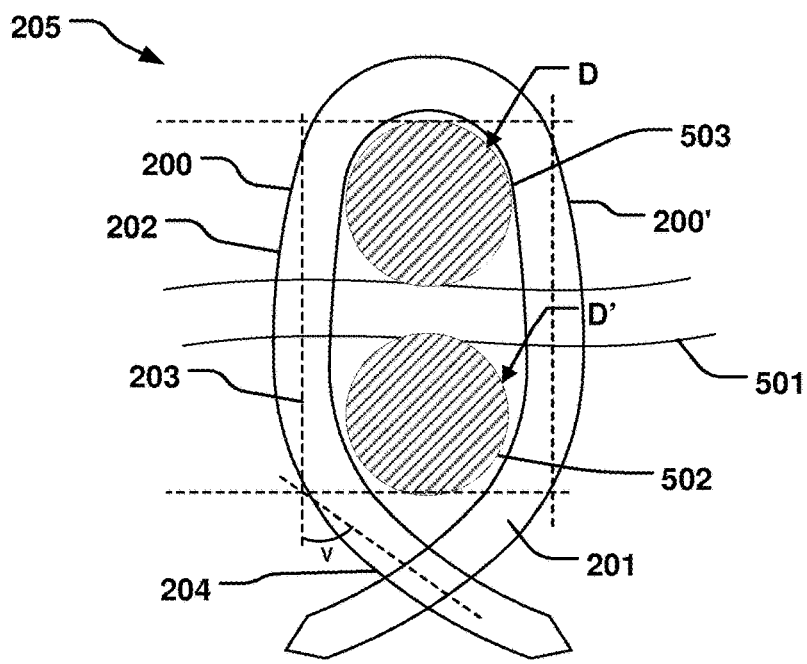
FIGS. 7a-b are illustration of a clip according to embodiments of the invention when positioned around an annuloplasty helix ring.

As seen in FIG. 7a, the clip 205 may be adapted to form a loop 201 around a first 502 and second 503 ring of a helix-shaped implant positioned on either side of heart valve tissue 501. The legs 200, 200', may in the relaxed shape, have a proximal portion 202 where the legs are substantially parallel along a proximal length 203 of the clip 205 corresponding to at least the sum of the diameters D, D', of the first and second rings 502, 503. The clip 205 has a distal portion 204 that has an angle (V) relative the proximal portion 202 so that the legs 200, 200' cross each other. The clip 205 thereby locks the ring efficiently in place at both sides of the valve. The clip 205 may thus have an oval or oblong shape, where the vertical portion of the open space inside the clip is substantially longer than the horizontal portion of approximating. The length of the proximal portion 202 is chosen so that the clip 205 reach across both the rings. The previously described clip 205 is disclosed according to one embodiment of the invention. The clip 205 may be used in any type of stapling device.

Figure 8A:
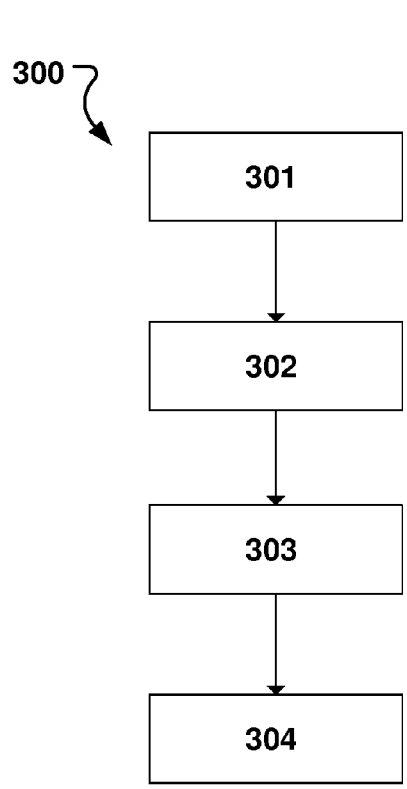
FIG. 8a is a flow chart illustrating a method of releasing a clip from a stapling device according to embodiments of the invention.

FIG. 8a illustrates a method 300 of releasing a clip 205 from a stapling device 100 comprising providing 301 a pre-loaded clip in the stapling device 100 having a sheath 101 and a clip guide 105, 105', at a distal end 102 of the sheath; moving 302 a pusher unit 103, 103', inside the sheath 101 from a proximal position to a distal position to engage the clip guide in which the clip is movable in a longitudinal direction 104 of the sheath. Moving the pusher to the distal position comprises moving 303 the clip guide from a closed (G) configuration, in which the clip guide is adapted to apply a restraining force on the clip so that the clip assumes a delivery shape (C), to an open configuration (G') in which the clip assumes a relaxed shape (C'), whereby when the clip is in the relaxed shape the clip is released 304 from the stapling device 100.

Figure 8B:
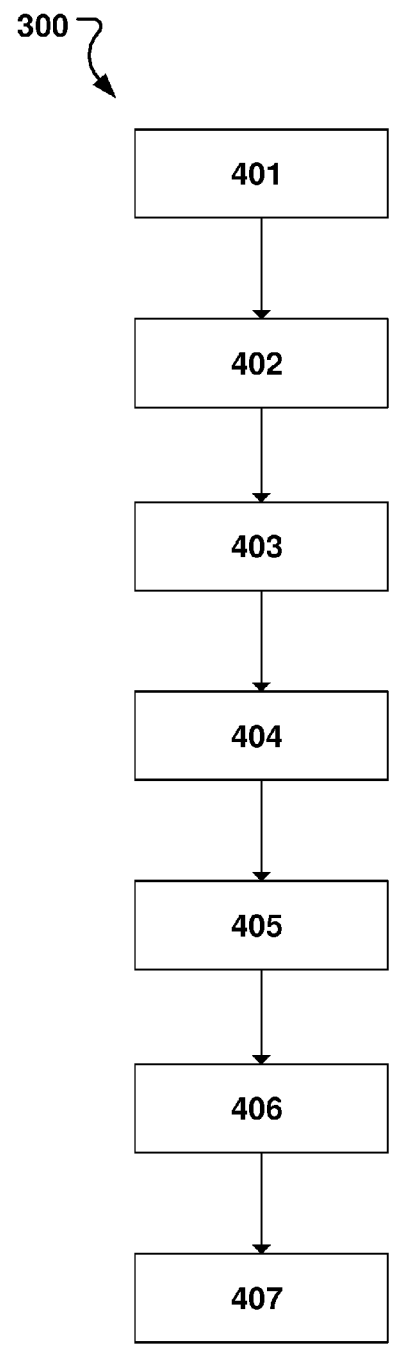
FIG. 8b is a flow chart illustrating a method of delivering a clip to a target site from a stapling device according to embodiments of the invention.

FIG. 8b illustrates a method 400 of delivering a clip 205 to a target site from a stapling device 100 as described above. The method 400 comprises providing 401 a pre-loaded clip in the stapling device having a sheath 101 and a clip guide 105, 105' at a distal end 102 of the sheath; navigating 402 the sheath to the target site such as a heart valve; attaching 403 a part of the clip to the target site for fixating tissue and/or fixating an implant, such as an annuloplasty ring to tissue; moving 404 a pusher unit 103, 103', inside the sheath from a proximal position to a distal position to engage the clip guide. Moving the pusher to the distal position comprises moving 405 the clip guide from a closed (G) configuration, in which the clip guide is adapted to apply a restraining force on the clip so that the clip assumes a delivery shape (C) for attaching said part of the clip, to an open configuration (G') in which the clip strives towards a relaxed shape (C') where legs 200, 200', of the clip has a crossed configuration. Moving the clip guide comprises attaching 406 a remaining part of the clip to the target site, and whereby when the remaining part of the clip is attached to the target site, the clip strives to the relaxed shape and applies a compressive force to the tissue and/or implant for fixating the tissue and/or implant, and releasing 407 the clip from the stapling device.

Figure 7B:
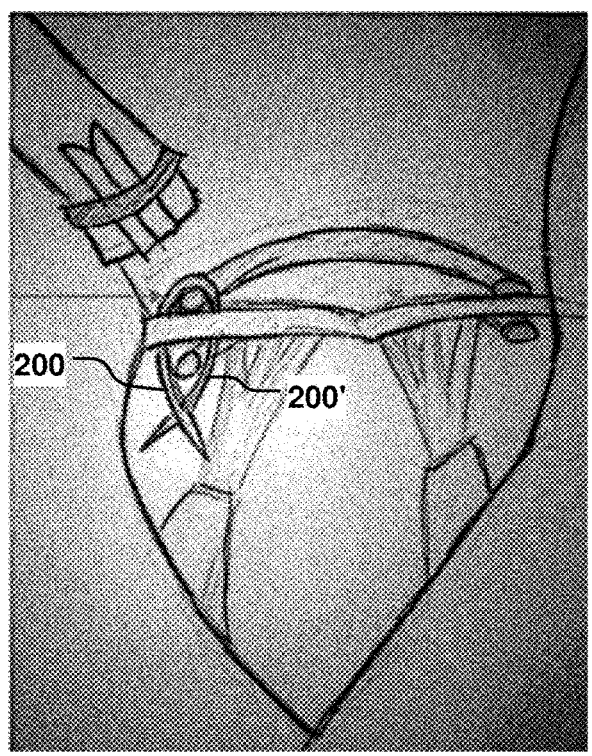

When said remaining part of the clip is attached to the tissue, legs 200, 200' of the clip may form a loop 201 around a first 502 and second ring 503 of a helix-shaped implant positioned on either side of heart valve tissue 501, as illustrated in FIGS. 7a-b.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A stapling device for attaching a clip to tissue, said stapling device comprising
   a sheath having a distal end for delivery of said clip,
   a pusher unit being movable inside said sheath along a longitudinal direction of said sheath, said distal end comprising a clip guide in which said clip is movable in said longitudinal direction,
   wherein said clip guide has a closed (G) configuration in which said clip guide is adapted to apply a restraining force on said clip so that said clip assumes a delivery shape (C) and an open (G') configuration in which said clip assumes a relaxed shape (C'),
   wherein said pusher unit is movable from a proximal position (P) in which said clip guide is in said closed configuration, to a distal position (P') in which said pusher unit engages said clip guide and the clip guide is in said open configuration,
   wherein said clip guide comprises a first clip guide element and a second clip guide element arranged at radially opposite peripheries of said sheath and extending in said longitudinal direction, and
   wherein said clip guide comprises two guide parts being separable in opposite directions (B, B') and in directions perpendicular to said longitudinal direction, wherein the separation of said two guide parts removes said restraining force on said clip so that said clip assumes said relaxed shape.

2. The stapling device according to claim 1, wherein said first clip guide or said second slip guide comprises a clip track being arranged to enclose a portion of a leg of said clip and to apply said restraining force and align said clip in said longitudinal direction when said clip guide is in said closed configuration.

3. The stapling device according to claim 1, wherein said pusher unit in said distal position separates said two guide parts in said opposite directions, whereby said clip guide assumes said open configuration.

4. The stapling device according to claim 1, wherein said two guide parts are separable in directions (B, B') of a tangent line to said sheath.

5. The stapling device according to claim 1, wherein said two guide parts each comprises a clip track arranged on either side of a leg of said clip to apply a restraining force and align said clip in said longitudinal direction when said clip guide is in said closed configuration.

6. The stapling device according to claim 1, wherein said clip guide is resiliently movable from said closed configuration to said open configuration.

7. The stapling device according to claim 6, comprising a resilient unit arranged to apply a resilient force on said clip guide.

8. The stapling device according to claim 1, wherein said first and second clip guides are arranged to enclose a portion of a first and a portion of a second leg of said clip, respectively, and align said clip in said longitudinal direction when said clip guide is in said closed configuration.

9. The stapling device according to claim 1, wherein each of said first and second clip guide elements comprises two separable guide parts.

10. The stapling device according to claim 9, wherein said pusher unit simultaneously engages said first and second clip guide elements when moved from said proximal position to said distal position, whereby said two separable guide parts of each of said first and second clip guide elements are separated to assume said open configuration.

11. A stapling kit comprising a stapling device according to claim 1 and a clip, said clip having legs and a delivery shape (C) in which said legs are substantially parallel, and a relaxed shape (C) wherein said legs cross each other.

12. A system comprising a stapling device according to claim 1 and a clip, said clip having legs and a delivery shape (C) in which said legs are substantially parallel, and a relaxed shape (C) wherein said legs cross each other, said system further comprising a helix-shaped implant having a first ring and a second ring, said rings being adapted for positioning on either side of heart valve tissue.

13. The system according to claim 12, wherein said clip is adapted to form a loop around the first ring and the second ring of said helix-shaped implant when said helix-shaped implant is positioned on opposite sides of heart valve tissue, whereby said legs, in a relaxed shape, have a proximal portion in which said legs are substantially parallel along a proximal length corresponding to at least a sum of the diameters (D, D') of said first and second rings, and a distal portion-that has an angle (V) relative said proximal portion so that said legs cross each other.

14. A stapling device for attaching a clip to tissue, said stapling device comprising
   a sheath having a distal end for delivery of said clip,
   a pusher unit being movable inside said sheath along a longitudinal direction of said sheath, said distal end comprising a clip guide in which said clip is movable in said longitudinal direction,
   wherein said clip guide has a closed (G) configuration in which said clip guide is adapted to apply a restraining force on said clip so that said clip assumes a delivery shape (C) and an open (G') configuration in which said clip assumes a relaxed shape (C'),
   wherein said pusher unit is movable from a proximal position (P) in which said clip guide is in said closed configuration, to a distal position (P') in which said pusher unit engages said clip guide and the clip guide is in said open configuration, wherein said clip guide comprises a first clip guide element and a second clip guide element arranged at radially opposite peripheries of said sheath and extending in said longitudinal direction, wherein said pusher unit comprises a distal tongue arranged to push said clip through said clip guide in said longitudinal direction and move said clip guide from said closed configuration to said open configuration, and wherein said distal tongue engages an angled surface of said clip guide relative said longitudinal direction when said pusher unit is moved from said proximal position to said distal position so that said clip guide is moved from said closed configuration to said open configuration.

15. The stapling device according to claim 14, wherein said distal tongue comprises an engagement surface having a recess to receive a portion of said clip.

16. A method of releasing a clip from a stapling device comprising, providing a pre-loaded clip in said stapling device having a sheath and a clip guide at a distal end of the sheath, moving a pusher unit inside said sheath from a proximal position to a distal position to engage said clip guide in which said clip is movable in a longitudinal direction of the sheath, wherein moving said pusher to said distal position comprises moving said clip guide from a closed configuration (G) in which said clip guide is adapted to apply a restraining force on said clip so that said clip assumes a delivery shape (C) to an open configuration (G') in which said clip assumes a relaxed shape (C) whereby, when said clip is in the relaxed shape, the clip is released from said stapling device, wherein said clip guide comprises a first clip guide element and a second clip guide element arranged at radially opposite peripheries of said sheath and extending in said longitudinal direction, and wherein said clip guide comprises two guide parts being separable in opposite directions (B, B') and in directions perpendicular to said longitudinal direction, wherein the separation of said two guide parts removes said restraining force on said clip so that said clip assumes said relaxed shape.

17. A method of delivering a clip to a target site from a stapling device said method comprising, providing a pre-loaded clip in said stapling device having a sheath and a clip guide comprising two guide parts separable in opposite directions (B,B') at a distal end of the sheath, navigating said sheath to a heart valve, attaching a part of said clip to said target site for fixating tissue and/or fixating an annuloplasty ring to tissue, moving a pusher unit inside said sheath from a proximal position to a distal position to engage said clip guide, wherein moving said pusher to said distal position comprises:

moving said clip guide from a closed (G) configuration in which said clip guide is adapted to apply a restraining force on said clip so that said clip assumes a delivery shape (C) for attaching a part of said clip, to an open configuration (G') in which said clip strives towards a relaxed shape (C) in which legs of said clip have a crossed configuration, wherein moving said clip guide comprises:

attaching a remaining part of said clip to said target site, and whereby when the remaining part of said clip is attached to said target site, said clip strives to said relaxed shape and applies a compressive force to said tissue and/or implant for fixating said tissue and/or implant, and releasing said clip from said stapling device by separating the two guide parts to remove said restraining force on said clip so that said clip assumes said relaxed shape.

18. The method according to claim 17, wherein when a remaining part of said clip is attached to said tissue, the legs of said clip form a loop around a first ring and a second ring of a helix-shaped implant positioned on opposite sides of a heart valve.

19. The method according to claim 17, further comprising engaging an angled surface of said clip guide when said pusher unit is moved from said proximal position to said distal position so that said clip guide is moved from said closed configuration to said open configuration.

20. A method of delivering a clip to a target site from a stapling device said method comprising, providing a pre-loaded clip in said stapling device having a sheath and a clip guide at a distal end of the sheath, navigating said sheath to a heart valve, attaching a part of said clip to said target site for fixating tissue and/or fixating an annuloplasty ring to tissue, moving a pusher unit inside said sheath from a proximal position to a distal position to engage an angled surface of said clip guide so that said clip guide is moved from a closed (G) configuration in which said clip guide is adapted to apply a restraining force on said clip so that said clip assumes a delivery shape (C) for attaching a part of said clip, to an open configuration (G') in which said clip strives towards a relaxed shape (C) in which legs of said clip have a crossed configuration, wherein moving said pusher to said distal position comprises:

wherein moving said clip guide comprises:

attaching a remaining part of said clip to said target site, and whereby when the remaining part of said clip is attached to said target site, said clip strives to said relaxed shape and applies a compressive force to said tissue and/or implant for fixating said tissue and/or implant and releasing said clip from said stapling device.

21. The method according to claim 20, wherein, when a remaining part of said clip is attached to said tissue, the legs of said clip form a loop around a first ring and a second ring of a helix-shaped implant positioned on opposite sides of a heart valve.

* * * * *